United States Patent [19]
Schutt

[11] Patent Number: 6,056,943
[45] Date of Patent: *May 2, 2000

[54] METHODS OF ULTRASOUND IMAGING USING PHOSPHOLIPID STABILIZED MICROBUBBLES

[75] Inventor: Ernest G. Schutt, San Diego, Calif.

[73] Assignee: Alliance Pharmaceutical Corp., San Diego, Calif.

[*] Notice: This patent is subject to a terminal disclaimer.

[21] Appl. No.: 09/092,351

[22] Filed: Jun. 5, 1998

Related U.S. Application Data

[63] Continuation of application No. 08/884,542, Jun. 27, 1997, which is a continuation of application No. 08/688,167, Jul. 29, 1996, Pat. No. 5,733,527, which is a continuation of application No. 08/314,074, Sep. 28, 1994, Pat. No. 5,540,909.

[51] Int. Cl.$^7$ ..................................................... A61B 8/13
[52] U.S. Cl. ................................................................ 424/9.52
[58] Field of Search ............................. 424/9.52; 600/458

[56] References Cited

U.S. PATENT DOCUMENTS

| | | | |
|---|---|---|---|
| 4,276,885 | 7/1981 | Tickner et al. ............................ | 128/660 |
| 4,466,442 | 8/1984 | Hilmann et al. .......................... | 128/653 |
| 4,613,326 | 9/1986 | Szwarc ....................................... | 604/89 |
| 4,657,756 | 4/1987 | Rasor et al. ............................... | 424/9 |
| 4,658,856 | 4/1987 | Rasot et al. ................................ | 424/9 |
| 4,684,479 | 8/1987 | D'Arrigo ................................... | 252/307 |
| 4,718,433 | 1/1988 | Feinstein .................................... | 128/660 |
| 4,774,958 | 10/1988 | Feinstein .................................. | 128/660.01 |
| 4,832,941 | 5/1989 | Berwing et al. ........................... | 424/9 |
| 4,844,882 | 7/1989 | Widder et al. ............................. | 424/9 |
| 4,898,734 | 2/1990 | Mathiowitz et al. ..................... | 424/426 |
| 4,904,479 | 2/1990 | Illum ......................................... | 424/490 |
| 4,925,678 | 5/1990 | Ranney ...................................... | 424/493 |
| 4,927,623 | 5/1990 | Long, Jr. .................................... | 424/5 |
| 4,957,656 | 9/1990 | Cerny et al. ............................... | 252/311 |
| 5,088,499 | 2/1992 | Unger ........................................ | 128/667.02 |
| 5,108,759 | 4/1992 | Ranney ...................................... | 424/493 |
| 5,123,414 | 6/1992 | Unger ........................................ | 128/654 |
| 5,141,738 | 8/1992 | Rasor et al. ............................... | 424/2 |
| 5,149,319 | 9/1992 | Unger ........................................ | 604/22 |
| 5,155,215 | 10/1992 | Ranney .................................... | 534/16 |
| 5,186,922 | 2/1993 | Shell et al. ................................ | 128/654 |
| 5,190,982 | 3/1993 | Erbel et al. ................................ | 521/56 |
| 5,195,520 | 3/1993 | Schlief et al. ............................. | 128/660.01 |
| 5,196,183 | 3/1993 | Yudelson et al. ......................... | 424/9 |
| 5,205,287 | 4/1993 | Erbel et al. ................................ | 128/632 |
| 5,205,290 | 4/1993 | Unger ........................................ | 128/653.4 |
| 5,255,683 | 10/1993 | Monaghan ............................... | 128/662.02 |
| 5,271,928 | 12/1993 | Schneider et al. ....................... | 424/9 |
| 5,305,757 | 4/1994 | Unger et al. ............................. | 128/662.02 |
| 5,310,540 | 5/1994 | Giddey et al. ............................ | 424/9 |
| 5,315,997 | 5/1994 | Widder et al. ........................... | 128/653.3 |
| 5,315,998 | 5/1994 | Tachibana et al. ....................... | 128/660.01 |
| 5,333,613 | 8/1994 | Tickner et al. ........................... | 128/662.02 |
| 5,334,381 | 8/1994 | Unger ....................................... | 424/9 |
| 5,348,016 | 9/1994 | Unger et al. ............................. | 128/662.02 |
| 5,352,435 | 10/1994 | Unger ...................................... | 424/9 |
| 5,352,436 | 10/1994 | Wheatley et al. ....................... | 424/9 |
| 5,376,380 | 12/1994 | Kikuchi et al. .......................... | 424/450 |
| 5,380,519 | 1/1995 | Schneider et al. ....................... | 424/9 |
| 5,393,524 | 2/1995 | Quay ........................................ | 424/9 |
| 5,409,688 | 4/1995 | Quay ........................................ | 424/9 |
| 5,410,516 | 4/1995 | Uhlendorf et al. ...................... | 367/7 |
| 5,413,774 | 5/1995 | Schneider et al. ...................... | 424/9.51 |
| 5,469,854 | 11/1995 | Unger et al. ............................ | 600/458 |
| 5,542,935 | 8/1996 | Unger et al. ............................ | 604/190 |
| 5,556,610 | 9/1996 | Yan et al. ................................ | 424/9.52 |
| 5,558,094 | 9/1996 | Quay ....................................... | 128/662.02 |
| 5,558,853 | 9/1996 | Quay ....................................... | 424/9.52 |
| 5,558,854 | 9/1996 | Quay ....................................... | 424/9.52 |
| 5,558,855 | 9/1996 | Quay ....................................... | 424/9.5 |
| 5,558,856 | 9/1996 | Klaveness et al. ..................... | 424/9.37 |
| 5,558,857 | 9/1996 | Klavenss et al. ....................... | 424/9.52 |
| 5,585,112 | 12/1996 | Unger et al. ............................ | 424/450 |
| 5,678,553 | 10/1997 | Uhlendorf et al. ..................... | 128/662.02 |
| 5,685,310 | 11/1997 | Porter ..................................... | 128/662.02 |
| 5,740,128 | 4/1998 | Hossack et al. ........................ | 367/138 |

FOREIGN PATENT DOCUMENTS

| | | |
|---|---|---|
| 652803B | 9/1994 | Australia . |
| 123235B1 | 10/1984 | European Pat. Off. . |
| 131540A2 | 1/1985 | European Pat. Off. . |
| 0230091 | 8/1987 | European Pat. Off. . |
| 231091A1 | 8/1987 | European Pat. Off. . |
| 0279379 | 8/1988 | European Pat. Off. . |
| 586875A1 | 2/1989 | European Pat. Off. . |
| 320433A3 | 6/1989 | European Pat. Off. . |
| 0357164 | 3/1990 | European Pat. Off. . |
| 0359246 | 3/1990 | European Pat. Off. . |
| 0554213 | 8/1993 | European Pat. Off. . |
| 606613A1 | 7/1994 | European Pat. Off. . |
| 633030A1 | 7/1994 | European Pat. Off. . |
| 0458745 | 9/1994 | European Pat. Off. . |
| 59-67229 | 4/1984 | Japan . |
| 8905160 | 6/1989 | WIPO . |
| 9109629 | 7/1991 | WIPO . |
| 9112823 | 9/1991 | WIPO . |
| 9115999 | 10/1991 | WIPO . |
| 9211873 | 7/1992 | WIPO . |
| 9222247 | 12/1992 | WIPO . |
| 9300930 | 1/1993 | WIPO . |

(List continued on next page.)

OTHER PUBLICATIONS

Sandra Hagen–Ansert, *Textbook of Diagnostic Ultrasonography*, pp. 10–12 ($2^{nd}$ ed. 1983).

Marc J. Ostro, *Liposomes From Biophysics to Therapeutics* pp. 2–8; 17–21; 74 and 105 ($1^{st}$ Ed. 1987).

Acoustic Non–Linearity Due to Micro–Bubbles in Water; Wesley & Safar, *Acustica,* 22: 177–182, 1969–70.

Ultrasonic Disruption; Alliger, Reprinted from *American Laboratory,* Oct. 1975.

Demonstration of Nonlinear Acoustical Effects at Biomedical Frequencies and Intensities; Carstensen, et al.

(List continued on next page.)

*Primary Examiner*—Gary E. Hollinden
*Attorney, Agent, or Firm*—Knobbe, Martens, Olson & Bear, LLP

[57] ABSTRACT

A method for ultrasonic harmonic imaging is disclosed, which uses microbubbles particularly selected for their properties of reradiating ultrasound energy at frequencies other than the exciting frequency.

39 Claims, No Drawings

FOREIGN PATENT DOCUMENTS

| | | |
|---|---|---|
| 9301712 | 2/1993 | WIPO . |
| 9302712 | 2/1993 | WIPO . |
| 9303671 | 3/1993 | WIPO . |
| 9305819 | 4/1993 | WIPO . |
| 9306869 | 4/1993 | WIPO . |
| 9325242 | 12/1993 | WIPO . |
| 9401140 | 1/1994 | WIPO . |
| 9406477 | 3/1994 | WIPO . |
| 9408707 | 4/1994 | WIPO . |
| 9409703 | 5/1994 | WIPO . |
| 9409829 | 5/1994 | WIPO . |
| 9416738 | 8/1994 | WIPO . |
| 9421175 | 9/1994 | WIPO . |
| 9428797 | 12/1994 | WIPO . |
| 9428939 | 12/1994 | WIPO . |
| 9628090 | 9/1996 | WIPO . |

OTHER PUBLICATIONS

*Ultrasound in Medicine & Biology,* 6: 159–168, 1980.

*Textbook of Diagnostic Ultrasonography,* Second Edition, by Sandra Hagen–Ansert, pp. 10–12, 1983.

Application of Ultrasonic Processors; Berliner, III *Biotechnology Laboratory,* 46–52, Mar. 1984.

Ultrasound Enhancement of Tissues During the Capillary Phase of PFOB—100% Immediately Post Infusion; Mattrey, M.D., "Abstract Association Of University Radiologists" 35$^{th}$ Annual Meeting, Mar. 22–27, 1987.

Perflurochemicals as US Contrast Agents for Tumor Imaging and Hepantosplenography: Preliminary Clinical Results; Mattery, M.D., Radiology, 163: 339–343, 1987.

Perflurooctylbromide: A New Contrast Agent for CT, Sonography, and MR Imaging; Mattrey, M.D. Manuscript 1988.

*Ultrasonics,* 30: No. 3, 95–103, 1992.

Simulated Capillary Blood Flow Measurement Using a Nonlinear Ultrasonic Contrast Agent, Schrope, et al., *Ultrasonic Imaging,* 14: 134–158, 1992.

*Liposomes, From Biophysics to Therapeutics,* Edited by Mark J. Ostro, Marcel Dukker Inc., New York, pp. 2–8, 17–21, 74 and 105.

*Foundation of Colloid Science,* vol. 1; Hunter, et al., Clarendon Press, Oxford, pp. 20 & 22.

Peripheral Vascular Doppler Examinations; Rae, II, *Textbook of diagnostic ultrasonsography,* pp. 323–325.

"Principles and Recent Developments in Ultrasound Contrast Agents"; N. de Jong, et al., *Ultrasonics,* 29:324–330, 1991.

"First Ultrasound Contrast Agent Awaits OK from FDA"; Greer, *Advance for Radiologic Science Professionals,* pp. 3–5, 1993.

Kitagawa, et al., *Biological Abstracts* 63:6392 (1977).

Keough, et al. *Biological Abstracts* 81: 105308 (1986).

Matsuda, et al. "Contrast Echocardiogrphy of the Left Heart by Intravenous Injection of Perfluorochemical Emulsion" *J. of cardiology* 13(4): 1021–1028 (1983).

Sunamotot, et al. "Liposomal Membrances" *J. Biochem.* 88:1219–1226 (1980).

Chapelon, et al. "Bubble Detection and Sizing with a Couble Frequency Doppler System" *Ultrasonics* 26: 148–154 (1988).

Cathignol, et al. "Bubble Sizing with High Spatial Resolution" IEEE Transactions on *Ultrasonics,* Ferroelectrics and Frequency Control 37(1): 30–37 (1990).

Miller, D.L. "Ultrasonic Detection of Resonant Cavitation Bubbles in a Flow tube by Their Second–Harmonic Emissions" *Ultrasonics:* 217–224 (1988).

Nakagawa, et al. "Imaging the Acoustic Nonlinearity Parameter with Finite–Amplitude Sound Waves . . . " *The Transactions of the IEICE* 71(8): 799–808 (1988).

1 Robert J. Hunter, *Foundations of Colloid Science* pp. 20 & 22 ($2^{nd}$ ed. 1989).

Goldberg et al., *Ultrasound in Med. & Biol.* 20: 319–333 (1994).

Schrope and Newhouse, *Ultrasound in Med. & Biol.* 19:567–579 (1993).

Mattrey, *Art, Cells, Blood Subs., and Immob. Biotech.* 22:295–313 (1994).

Peter N. Burns, *Radiologica Medica* 87:71–82 (Suppl. 1 al. n. 5, 1994).

METHODS OF ULTRASOUND IMAGING USING PHOSPHOLIPID STABILIZED MICROBUBBLES

This application is a continuation of patent application Ser. No. 08/884,542 filed on Jun. 27, 1997, which is a continuation of U.S. patent application Ser. No. 08/688,167 filed Jul. 29, 1996, now U.S. Pat. No. 5,733,527 which is a continuation of U.S. patent application Ser. No. 08/314,074 filed Sep. 28, 1994, now U.S. Pat. No. 5,540,909.

BACKGROUND OF THE INVENTION

1. Field of the Invention

The present invention relates to an improved method for harmonic ultrasound imaging using a contrast agent specially designed to return harmonic frequencies.

2. Background of the Art

Ultrasound technology provides an important and more economical alternative to imaging techniques which use ionizing radiation. While numerous conventional imaging technologies are available, e.g., magnetic resonance imaging (MRI), computerized tomography (CT), and positron emission tomography (PET), each of these techniques use extremely expensive equipment. Moreover, CT and PET utilize ionizing radiation. Unlike these other technologies, ultrasound imaging equipment is relatively inexpensive. Moreover, ultrasound imaging does not use ionizing radiation.

In using the ultrasound technique, sound waves are transmitted into an object or patient via a transducer. As the sound waves propagate through the object or body, they are either reflected or absorbed by tissues and fluids. Reflected sound waves are detected by a receiver and processed to form an image. The acoustic properties of the tissues and fluids determine the contrast which appears in the resulting image.

Ultrasound imaging therefore makes use of differences in tissue density and composition that affect the reflection of sound waves by those tissues. Images are especially sharp where there are distinct variations in tissue density or compressibility, such as at tissue interfaces. Interfaces between solid tissues, the skeletal system, and various organs and/or tumors are readily imaged with ultrasound.

Accordingly, in many imaging applications ultrasound performs suitably without use of contrast enhancement agents; however, for other applications, such as visualization of flowing blood in tissues, there have been ongoing efforts to develop agents to provide contrast enhancement. One particularly significant application for such contrast agents is in the area of vascular imaging. Such ultrasound contrast agents could improve imaging of flowing blood in the heart, kidneys, lungs, and other tissues. This, in turn, would facilitate research, diagnosis, surgery, and therapy related to the imaged tissues. A blood pool contrast agent would also allow imaging on the basis of blood content (e.g., tumors and inflamed tissues) and would aid in the visualization of the placenta and fetus by enhancing only the maternal circulation.

A variety of ultrasound contrast enhancement agents have been proposed. The most successful agents have generally consisted of microbubbles that can be injected intravenously. In their simplest embodiment, microbubbles are miniature bubbles containing a gas, such as air, and are formed through the use of foaming agents, surfactants, or encapsulating agents. The microbubbles then provide a physical object in the flowing blood that is of a different density and a much higher compressibility than the surrounding fluid tissue and blood. As a result, these microbubbles can easily be imaged with ultrasound.

However, contrast agents developed thus far for use in ultrasound imaging have various problems. Contrast agents containing aqueous protein solutions require use of a foreign protein which may be antigenic and potentially toxic. Liposomal contrast agents, consisting of liposomes having gas encapsulated therein, present problems due to uneven size distribution and poor stability. Many of the existing contrast agents have failed to provide improved imaging, and furthermore, many of the methods used to prepare the contrast agents are inefficient, expensive, and otherwise unsatisfactory.

Conventional ultrasound systems work by transmitting pulses of ultrasound of a given frequency and measuring the time interval between this transmission and the detection of the reflected echoes from within the object or body being imaged. Large numbers of microbubbles behave collectively as a large reflector. The system relies on measurement of reflected sound waves of the same frequency as that transmitted to produce the image.

It has been found to be advantageous, especially in biological applications, to detect or image an ultrasound contrast agent while suppressing the ultrasound signal reflected by other objects such as tissue and bone (see Williams et al., WO 91/15999). The ability to image ultrasound contrast agent bubbles in the blood by detecting harmonic frequencies in the echo when they are excited by an ultrasound beam at a different frequency (the fundamental) greatly increases the sensitivity of contrast agent detection by ignoring the background fundamental frequency signal scattered by other non-bubble objects in the organism, much like the detection of fluorescent dyes by their frequency-shifted light is inherently more sensitive than the detection of light-absorbing dyes by their modulation of the illuminating light intensity. Unlike microbubbles, animal tissues return very little harmonic frequencies. Thus, background imaging is substantially eliminated through harmonic imaging.

As existing contrast enhancing agents and methods for ultrasound imaging have not been found to be entirely satisfactory, there is a substantial need for providing an improved ultrasound contrast agent and method of ultrasound imaging which results in the production of improved ultrasound images.

SUMMARY OF THE INVENTION

In accordance with one aspect of the present invention, there is provided a method of ultrasonic harmonic imaging using ultrasonic energy transmitted by an ultrasonic source to an object or body to be imaged. The method comprises introducing into the object or body a contrast agent comprising microbubbles having generally spherical membranes and containing gaseous material having vapor pressure at 37° C. over 23 mmHg, less than about 1% wt./wt. solubility/miscibility in water, concentration in gas phase when detected greater than 2% mole fraction, and a concentration greater than 50% of its saturation concentration. At least a portion of said object or body is then ultrasonically imaged.

Preferably, the gaseous material contained in the bubbles is selected from the group consisting of perfluorohexane, perfluoropentane, perfluorocyclopentane, 1,1,2-trichlorotrifluoroethane, sulfur hexafluoride, cyclopentane, methylene chloride, pentane and hexane. Preferably, the concentration in gas phase when detected is 25%, or 100%. In a preferred embodiment, the membranes comprise a surfactant.

In accordance with another aspect of the present invention, there is provided a method of ultrasonic harmonic imaging using ultrasonic energy transmitted by an ultrasonic source to an object or body to be imaged, comprising introducing into said object or body a contrast agent comprising microbubbles. These microbubbles have generally spherical membranes and contain material that comprises at least 2% mole fraction of a gas that has a solubility of its liquid phase in hexane at 37° C. of more than about 10% mole/mole and a water solubility/miscibility of its liquid phase of less than about 1% wt./wt. in water at 37° C. At least a portion of the object or body is then ultrasonically imaged.

In a preferred embodiment, the gas is a hydrocarbon or a fluorocarbon. More preferably, the gas is selected from the group consisting of perfluorohexane, perfluoropentane, perfluorocyclopentane, 1,1,2-trichlorotrifluoroethane, sulfur hexafluoride, cyclopentane, methylene chloride, pentane, hexane, dichlorodifluoromethane, trichloromonofluoromethane, perfluorobutane, perfluorocyclobutane, perfluoropropane, butane, cyclobutane, propane, methane, and ethane.

Preferably, the membranes comprise a surfactant. The surfactant is preferably fluorinated. In another preferred embodiment, the material contained in the microbubbles comprises at least about 25% mole fraction of said gas, or about 100% mole fraction of said gas.

In accordance with yet another embodiment of the present invention, there is provided a method of ultrasonic harmonic-imaging using ultrasonic energy transmitted by an ultrasonic source to an object or body to be imaged, comprising introducing into the object or body a contrast agent comprising microbubbles stabilized with at least one surfactant. At least a portion of the object or body is then ultrasonically imaged.

In a preferred embodiment, the surfactant will change the surface tension of water by more than 5 dynes/cm when the area per molecule of surfactant has changed by 10% as measured on a Langmuir film balance. In another preferred embodiment, the surfactant has a component having a hydrophilic-lipophilic balance less than 11, or less than or equal to 8. In yet another preferred embodiment, the surfactant has a component with a molecular weight over 1,000 and capable of lowering the surface tension of water to 40 dynes/cm or lower. In still another preferred embodiment, the surfactant is capable of lowering the surface tension of water to 40 dynes/cm or lower and has a critical micelle concentration of 0.3 or less volume fraction in water. Preferably, the surfactant is non-Newtonian.

In accordance with still another aspect of the present invention, in a method for ultrasonic harmonic imaging of an object or body comprising introducing into the object or body a contrast agent and transmitting ultrasonic energy from an ultrasonic source to the object or body and detecting radiated energy from the object or body, there is provided the improvement comprising the contrast agent being comprised of microbubbles having the property of radiating imageable ultrasonic energy at a frequency which is different from that transmitted by the ultrasonic source that is independent of the resonant frequency of the bubble. In this method, the detecting step utilizes a different frequency than the transmitting step.

In a preferred embodiment, the microbubbles contain a gas or gas mixture, and the microbubbles are stabilized by their gas or gas mixture contents. In another preferred embodiment, the microbubbles are produced by spray drying a liquid formulation containing a biocompatible membrane-forming material to form a microsphere powder therefrom, combining the microspheres with a gas osmotic agent, and mixing an aqueous phase with the powder. The powder substantially dissolves in the aqueous phase to form microbubbles. Preferably, the microbubbles are coated with a monolayer of surfactant.

In accordance with yet another aspect of the present invention, there is provided in method for harmonic ultrasound imaging utilizing microbubbles, the improvement comprising providing at least one hydrocarbon gas or fluorocarbon gas in the microbubbles in a concentration of at least 2% mole fraction.

DETAILED DESCRIPTION OF THE INVENTION

Introduction

As used in the present description and claims, the terms "vapor" and "gas" are used interchangeably. Similarly, when referring to the tension of dissolved gas in a liquid, the more familiar term "pressure" may be used interchangeably with "tension." "Gas osmotic pressure" is more fully defined below, but in a simple approximation can be thought of as the difference between the partial pressure of a gas inside a microbubble and the pressure or tension of that gas (either in a gas phase or dissolved in a liquid phase) outside of the microbubble, when the microbubble membrane is permeable to the gas. More precisely, it relates to differences in gas diffusion rates across a membrane. The term "membrane" is used to refer to the material surrounding or defining a microbubble, whether it be a surfactant, another film forming liquid, or a film forming solid or semisolid. "Microbubbles" are considered to be bubbles having a diameter between about 0.5 and 300 $\mu$m, preferably having a diameter no more than about 200, 100, or 50 $\mu$m, and for intravascular use, preferably not more than about 10, 8, 7, 6, or 5 $\mu$m (measured as average number weighted diameter of the microbubble composition). When referring to a "gas," it will be understood that mixtures of gases together having the requisite property fall within the definition, except where the context otherwise requires.

The present invention provides a method for harmonic ultrasound imaging using specially designed microbubbles as ultrasound contrast enhancement agents. By optimizing the ability of these gas bubbles to transform the frequency of the ultrasonic radiation to which they are subjected (the fundamental), imaging is enhanced.

When a gas bubble is exposed to high pressure amplitude ultrasound, which is not practical in biological systems because of cavitation and cell tissue damage, or is exposed to low amplitude exciting ultrasound energy near the resonant frequency of the bubble, it acts in a nonlinear fashion. That is, the change in bubble volume is no longer proportional to the change in pressure of its surroundings. This nonlinear behavior generates components of the reradiated ultrasound energy that are at frequencies other than the exciting frequency. See Eatock, *J. Soc. Acoust. Am.* 77:1692–1701 (1985); de Jong et al., *Ultrasonics*, 29:324–330 (1991); and Miller, *Ultrasonics*, (1981). These harmonics at frequencies both above and below the incident frequency are the result of the mechanics of motion for the system. At medically useful ultrasound exciting amplitudes, significant harmonics are only generated by bubbles within a narrow size range containing the resonant diameter. For example, for a 3 megahertz excitation frequency, an air bubble in water with a diameter of 1.1 micron will resonate and generate harmonics, but the amplitude of these harmonics will drop by a factor of 2 for diameters only 12% different from the resonant diameter. Bubbles in this size range are only a small fraction of the relatively broad size distribution of most microbubbles (de Jong et al., *Ultrasonics* 30(2):95–103 (1992)). Bubbles produced with solid or semisolid shells e.g., denatured albumin (described in U.S. Pat. No. 4,957,656; de Jong et al., *Ultrasonics* 30(2):95–103 (1992); and de Jong, *Acoustic Properties of Ultrasound Contrast Agents,* Ph.D. thesis, Erasmus University, Rotterdam (1993)) exhibit increased damping due to the viscous shell and thus do not have the large radius excursions at resonance required to produce significant harmonic components in the scattered (reradiated) signal. Thus, the present invention advantageously provides for the use of microbubbles capable of generating harmonics at medically useful ultrasound exciting amplitudes.

To detect the reradiated ultrasound energy generated by the microbubbles, the present invention makes use of a modified conventional ultrasound scanner system. The system is able to detect or select one or more of the new frequencies, or harmonics, radiated by the microbubbles for production of the ultrasound image. In other words, it detects a frequency different from the emitted frequency. Equipment suitable for harmonic ultrasound imaging is disclosed in Williams et al., WO 91/15999. Many conventional ultrasound imaging devices, however, utilize transducers capable of broad bandwidth operation, and the outgoing waveform sent to the transducer is software controlled. For this reason, reprogramming to emit a waveform different from the one detected is well within the level of skill in the art.

In practicing the present invention, the parameters of the ultrasound transmitted (e.g., the frequency, pulse duration, and intensity) can be varied according to the particular circumstances, and the optimal parameters for any particular case can be readily determined by one of ordinary skill in the art.

While bubbles have been shown to be the most efficient ultrasound scatterers for use in intravenous ultrasound contrast agents, the contrast enhancement agents of the present invention provide unexpectedly superior imaging; for example, clear, vivid, and distinct images of blood flowing through the heart and kidneys are achieved. The present invention is particularly suited for study of blood flow, but is equally applicable to the study of other liquids or tissues as well. Small, nontoxic doses can be administered in a peripheral vein or lymph vessel and used to enhance images of all or part of the body. Cavities or areas within a body into which microbubbles can be introduced can be imaged according to the method of the present invention. Thus, the present invention provides means for imaging a variety of body cavities and vasculature which may be difficult to image using conventional techniques.

It is not essential that the subject being imaged be an organic tissue. Rather, the method of the present invention can be used to image anything containing spaces into which the contrast agent can be introduced, so long as the material surrounding the contrast agent is permeable to the ultrasonic radiation and does not itself resonate in a manner which obscures the selected harmonic of the microbubbles and does not hinder the resonance of the microbubbles.

The method of the present invention may use the measurement of a single received frequency, different from that of the frequency originally transmitted, to form a single image. Alternatively, several different frequencies different from that of the exciting frequency can be detected and used to create multiple images, which can be viewed separately or electronically processed into a composite image.

The received frequency or frequencies can be processed by a variety of methods well known to one of ordinary skill in the art. These include, for example, making the receiving transducer selective toward the desired harmonic or harmonics so that it ignores the fundamental, or by using software or hardware filters to separate or isolate the various frequencies.

Microbubble Properties

It was surprisingly discovered that certain properties of microbubble ultrasound contrast agents can enhance their ability to produce harmonics. While bubbles have been shown to be the most efficient ultrasound scatterers for use in intravenous ultrasound contrast agents, one practical drawback is the extremely short lifetime of the small (typically less than 5 microns diameter) bubbles required to pass through capillaries in suspension. This short lifetime is caused by the increased gas pressure inside the bubble, which results from the surface tension forces acting on the bubble. This elevated internal pressure increases as the diameter of the bubble is reduced. The increased internal gas pressure forces the gas inside the bubble to dissolve, resulting in bubble collapse as the gas is forced into solution. The LaPlace equation, $\Delta P = 2\gamma/r$, (where $\Delta P$ is the increased gas pressure inside the bubble, $\gamma$ is the surface tension of the bubble film, and r is the radius of the bubble) describes the pressure exerted on a gas bubble by the surrounding bubble surface or film. The LaPlace pressure is inversely proportional to the bubble radius; thus, as the bubble shrinks, the LaPlace pressure increases, increasing the rate of diffusion of gas out of the bubble and the rate of bubble shrinkage.

It has been discovered that gases and gas vapor mixtures which can exert a gas osmotic pressure opposing the LaPlace pressure can greatly retard the collapse of these small diameter bubbles (see U.S. Pat. No. 5,605,673, and U.S. Pat. No. 5,639,443, incorporated herein by reference). Those inventions include use of a primary modifier gas or mixture of gases that dilutes a gas osmotic agent to a partial pressure less than the gas osmotic agent's vapor pressure. The gas osmotic agent or agents are generally relatively hydrophobic and relatively bubble membrane impermeable and also further possess the ability to develop gas osmotic pressures greater than 75 or 100 mmHg at a relatively low vapor pressure. The gas osmotic agent or agents act to regulate the osmotic pressure within the bubble. Through regulating the osmotic pressure of the bubble, the gas osmotic agent (defined herein as a single or mixture of chemical entities) exerts pressure within the bubble, aiding in preventing collapse of the bubble.

Bubbles of air saturated with selected perfluorocarbons can grow rather than shrink when exposed to air dissolved in a liquid due to the gas osmotic pressure exerted by the perfluorocarbon vapor. The perfluorocarbon vapor is relatively impermeable to the bubble film and thus remains inside-the bubble. The air inside the bubble is diluted by the perfluorocarbon, which acts to slow the air diffusion flux out of the bubble. This gas osmotic pressure is proportional to the concentration gradient of the perfluorocarbon vapor across the bubble film, the concentration of air surrounding the bubble, and the ratio of the bubble film permeability to air and to perfluorocarbon.

As discussed above, the LaPlace pressure is inversely proportional to the bubble radius; thus, as the bubble shrinks, the LaPlace pressure increases, increasing the rate of diffusion of gas out of the bubble and the rate of bubble shrinkage, and in some cases leading to the condensation and virtual disappearance of a gas in the bubble as the combined LaPlace and external pressures concentrate the osmotic agent until its partial pressure reaches the vapor pressure of liquid osmotic agent.

Conventional microbubbles that contain any single gas will subsist in the blood for a length of time that depends primarily on the arterial pressure, the bubble diameter, the membrane permeability of the gas through the bubble's surface, the mechanical strength of the bubble's surface, the presence, absence, and concentration of the gases that are ordinarily present in the blood or serum, and the surface tension present at the surface of the bubble (which is primarily dependent on the identity and concentration of the surfactants which form the bubble's surface). Each of these parameters are interrelated, and they interact in the bubble to determine the length of time that the bubble will last in the blood.

It was surprisingly discovered that when the bubble contains a vapor which can condense at useful temperatures (e.g., 37° C. for humans) and pressure, the change of phase, from gas or vapor to a liquid, causes the volume of the bubble to change much more rapidly than the change expected for linear systems. This nonlinearity results in the generation of harmonics. For this effect to be significant, the vapor must be present in the gas phase of the bubble at a mole fraction concentration of greater than approximately 2%, and preferably at about 5%, 10%, 25%, 50%, or 100%. The vapor inside the bubble is preferably near saturation under the conditions of examination, preferably at least about 50%, 75% or 100% of the saturation concentration. Thus, for microbubbles used for imaging in a human, the liquid phase of the vapor in the bubble must have a vapor pressure at 37° C. greater than 2% of the pressure inside the bubble (one atmosphere plus the blood pressure of the human being examined plus the pressure caused by the surface tension of the bubble, the LaPlace pressure). This total pressure for 3 micron bubbles could reach 1.5 bar and thus requires the liquid phase of the vapor in the bubble to have a vapor pressure at 37° C. greater than approximately 23 mmHg. The liquid phase of the vapor should also have a low solubility in water, preferably less than 1% wt./wt. Vapors of materials such as perfluorohexane, perfluoropentane, perfluorocyclopentane, 1,1,2 trichlorotrifluoroethane (FREON 113; EM Science, Gibbstown, N.J.), sulfur hexafluoride, cyclopentane, methylene chloride, pentane and hexane are particularly suitable.

While condensation of a vapor diluted with other gases involves diffusion of the gas to the forming film of liquid and thus requires a finite time to complete condensation, the fraction of vapor near the surface of the body temperature water surrounding the bubble can condense rapidly in less than the microsecond time frame of diagnostic ultrasound. A bubble containing pure vapor, e.g., perfluoropentane, can nearly instantly condense much like the water vapor bubbles that occur during high intensity ultrasound cavitation. These cavitation bubbles are known to produce high intensity harmonics, (see Welsby et al., Acustica 22: 177–182 (1969), although at biologically toxic intensities for water vapor bubbles.

The change of phase resulting in increased harmonic generation as described above can also occur when a gas is dissolved in or adsorbed to the hydrophobic regions of the surfactants at the bubble surface. This adsorption or dissolution equilibrium is effected by the partial pressure of the gas inside the bubble and thus by the total pressure inside the bubble. An increase in pressure applied by the exciting ultrasound beam will shift the equilibrium toward dissolution or adsorption in the surfactant layer, causing a volume change different from that expected from a linear system.

Suitable gases are ones that have a solubility/miscibility of their liquid forms with hexane, which is a model for the hydrophobic region of surfactants, of greater than 10% mole/mole at 37° C. For gases with a boiling point below 37° C., e.g. butane and perfluorobutane, this measurement must be carried out at elevated pressure. The adsorbing gas should be present in the bubble gas phase at a concentration of more than 2% by mole fraction of the gas mixture and preferably at about 5%, 10%, 25%, 50%, or 100%. The use of fluorinated surfactants with fluorinated gases is preferred. The liquid phase of the adsorbing gas should be relatively insoluble in water, less than 1% wt./wt. solubility/miscibility.

Previous treatments of the mechanics of bubbles excited by ultrasound treat the surface tension of the bubble as a constant while the bubble expands and contracts. The surface tension at the surface of a small bubble significantly effects the pressure inside the bubble as defined by the law of LaPlace wherein the pressure inside a bubble (above the external ambient) is inversely proportional to the diameter of the bubble and proportional to the surface tension of the surfactant film. For example, a 3 micron bubble with a surface tension of 40 dynes/square centimeter has an internal pressure more that one quarter bar above its surroundings. Some surfactants are non-Newtonian, that is, their surface tension changes rapidly when the surfactant layer is compressed, as measured in a standard Langmuir trough. The change in surface tension of a surfactant film, as the surface area is changed, is quantitatively characterized by the Surface Dilation Modulus. This is defined as:

$$E = \frac{-d\gamma}{d\ln A}$$

where E is the surface dilation modulus, $d\gamma$ is the change in surface tension, and $d\ln A$ is the change in the natural log of the surface area. The additional change in surface tension due to the rate of area change is characterized by the Surface Dilational Viscosity. This is defined as:

$$\Delta\gamma = K \frac{1}{A} \frac{dA}{dt}$$

where $\Delta\gamma$ is the change in surface tension, K is the surface dilational viscosity, A is the area of surfactant film surface, and dA/dt is the rate of change of the surfactant film surface area (see Adamson, *Physical Chemistry of Surfaces,* 5th ed., John Wiley & Sons, Inc. New York, 1990).

When a bubble is formed employing a non-Newtonian surfactant, its surface tension, and therefore its internal pressure will change as the surface area of the bubble changes in response to the exciting ultrasound pressures. This additional expansion and contraction in response to changes in surface tension leads to a more nonlinear compressibility and therefore the generation of a higher intensity of harmonics. The expanding bubble increases the surface area of the surfactant film until the rising surface tension opposes further expansion. The compressing bubble, during the high pressure part of the exciting ultrasound cycle, will reduce the bubble surface area until the surface tension abruptly decreases, limiting further compression and distorting the sinusoidal volume change waveform, causing harmonics to be generated.

Suitable surfactants for use in the present invention are any surfactant or mixture, hydrocarbon or fluorinated, that has a component that will change the surface tension of water by more than 5 dynes/cm when the area per molecule of surfactant has changed by 10% as measured on a Langmuir film balance.

Other suitable surfactants are those surfactants with a component having a hydrophilic-lipophilic balance less than 11, preferably less than or equal to 8.

High molecular weight surfactants (e.g. over 1,000) diffuse slowly compared to the microsecond timeframe of ultrasound, and thus surfactants with a component with a molecular weight over 1,000 and capable of lowering the surface tension of water to 40 dynes/cm or lower are suitable independent of the above.

Considering diffusion, solubility and microsecond time scales, other suitable surfactants include any surfactant capable of lowering the surface tension of water to 40 dynes/cm or lower and having a CMC (critical micelle concentration) of 0.3 or lower volume fraction in water.

Examples of surfactants for use in the present invention include undenatured human albumin, phospholipids (e.g. phosphatidyl choline), sugar esters (e.g. sucrose stearate, sucrose distearate, sucrose tristearate), block copolymers (PLURONIC F-68, PLURONIC P-123), ZONYL fluorosurfactants available from E.I. Du Pont (e.g. FSK, FSC, FSO, FSN, FSE, FSP, FSA, FSJ, UR, TBS) fatty acids (e.g. stearic acid, oleic acid) and their salts (e.g. sodium stearate, potassium oleate).

With these particular operating constraints in mind, suitable microbubbles of the first type (containing a gas that partially condenses upon bubble excursion) may advantageously comprise perfluorohexane, perfluoropentane, perfluorocyclopentane, 1,1,2 trichlorotrifluoroethane (FREON 113; EM Science, Gibbstown, N.J.), sulfur hexafluoride, cyclopentane, methylene chloride, hexane and pentane. Similarly, suitable microbubbles of the second type (gas soluble in surfactant) may advantageously comprise perfluorohexane, perfluoropentane, perfluorocyclopentane, 1,1,2 trichlorotrifluoroethane (FREON 113; EM Science, Gibbstown, N.J.), sulfur hexafluoride, cyclopentane, methylene chloride, hexane, pentane, perfluorobutane, perfluorocyclobutane, perfluoropropane, FREON 12 (dichlorodifluoromethane), FREON 11 (trichloromonofluoromethane), butane, cyclobutane, propane, methane, and ethane.

Bubbles that are stabilized by viscous shells (eg. denatured protein gel, U.S. Pat. No. 4,957,656; saturated sugar solutions, U.S. Pat. Nos. 5,141,738 and 4,657,756) damp the oscillation of the bubble at resonance and thus prevent the large volume excursions required to produce harmonics (de Jong et al., *Ultrasonics*, 29:324–330 (1991); de Jong et al., *Ultrasonics* 30(2):95–103 (1992); and de Jong, *Acoustic Properties of Ultrasound Contrast Agents*, Ph.D. thesis, Erasmus University, Rotterdam (1993)). A bubble stabilized by its gas phase contents as discussed above (e.g., a material such as a highly fluorinated compound such as perfluorohexane, perfluoropentane, perfluorobutane) requires only a monomolecular layer (monolayer) of surfactant to make it stable in the bloodstream long enough for practical utility (see U.S. Pat. No. 5,605,673; U.S. Pat. No. 5,639,443; and Quay, PCT/US92/07250 and PCT/US94/00422). Thus both at resonance and away from resonance, a bubble stabilized by its gas contents and with a monolayer of surfactant on its surface, has less damping to dissipate the exciting energy of the exciting ultrasound pressure waves and thus undergoes larger volume excursions to reradiate or scatter more of its energy as harmonic components at frequencies other than the excitation frequency. Sucrose stearate and PLURONIC F-68 are two examples of surfactants which coat microbubbles with a monolayer and thus do not damp the gas/vapor stabilized bubble's oscillations.

With these particular parameters in mind, the particulars of construction of suitable microbubbles will be set forth below.

In addition to the particularly described microbubbles, other microbubbles, such as those described in Quay, PCT/US92/07250 and PCT/US94/00422, may be used, provided that the gas and/or surfactant is selected as described herein such that harmonic reradiation is sufficient for use in the present invention.

Microbubble Construction

A. The Membrane-Forming Liquid Phase

The external, continuous liquid phase in which the bubble resides typically includes a surfactant or foaming agent. Surfactants suitable for use in the present invention include any compound or composition that aids in the formation and maintenance of the bubble membrane by forming a layer at the interface between the phases, and having the criteria discussed above. The foaming agent or surfactant may comprise a single compound or any combination of compounds, such as in the case of co-surfactants.

It will be appreciated that a wide range of surfactants can be used. Indeed, virtually any surfactant or foaming agent (including those still to be developed) capable of facilitating formation of the microbubbles and having the properties discussed above can be used in the present invention. The optimum surfactant or foaming agent or combination thereof for a given application can be determined through empirical studies that do not require undue experimentation. Consequently, one practicing the art of the present invention should choose the surfactant or foaming agents or combination thereof based upon such properties as biocompatibility, solubility of gas phase in surfactant, and their non-Newtonian behavior.

B. The Gas Phase

A major aspect of the present invention is in the selection of the gas phase. As was discussed above, the present invention relies on the use of microbubbles which have the ability to generate harmonics of the originally transmitted ultrasound frequency. Such microbubbles can contain a gas or combination of gases to harness or cause differentials in partial pressures and to generate gas osmotic pressures which stabilize the bubbles. Further, the microbubbles contain materials which can change state from a gas to a liquid or solid at body temperature, (generally from about 35.5° C. to about 40° C.), and at useful pressures (generally about 1–2 atm). Alternatively, the microbubbles can contain material which adsorbs or solubilizes in the hydrophobic portion of the bubble membrane as discussed above.

Accordingly, fluorocarbons or other compounds that are not gases at room or body temperature can be used, provided that they have sufficient vapor pressure, preferably at least about 10–20 mmHg, and more preferably 30, 40, 50 or 100 mmHg at body temperature, or more preferably at least about 150 or 200 mmHg. However, with the first type of microbubble (condensing gas), the vapor pressure of at least one of the components should be below about 900 or 1000 mmHg, such that when a sufficient concentration of the gas is present in a bubble, the absolute pressure applied to the gas in the bubble during imaging exceeds the vapor pressure of that component divided by the fractional partial pressure provided in the bubble by that gas. Thus, $P_A < P_V/P_{PF}$, where $P_A$ is the absolute pressure in the bubble when compressed by an ultrasound wave, $P_V$ is the vapor pressure at body temperature of the relevant gaseous compound, and $P_{PF}$ is the partial. pressure of that gas expressed as a fraction of the total gas pressure in the bubble. For example, if the pressure in the bubble is 1000 mmHg (760 mmHg atmospheric pressure plus 100 mmHg contributed by systolic pressure plus a momentary 140 mmHg contributed by sonic compression) then a condensing gas contributing 50% of the partial gas pressure in the bubble should have a vapor pressure at body temperature of under 500 mmHg.

As suggested above, fluorocarbon gases are particularly preferred. The term fluorocarbon as used herein includes fully fluorinated compounds (perfluorocarbons) as well as partially fluorinated hydrocarbon/fluorocarbon materials, all unsubstituted or substituted with another halogen such as Br, Cl, or F or another substituent, such as O, OH, S, NO, and the like. Substances possessing suitable solubility and/or vapor pressure criteria include perfluorohexane, perfluoropentane, perfluorocyclopentane, perfluorobutane, perfluorocyclobutane, and perfluoropropane.

It will be appreciated that one of ordinary skill in the art can readily determine other compounds that would perform suitably in the present invention that do not meet both the solubility and vapor pressure criteria, described above. Rather, it will be understood that certain compounds can be considered outside the preferred range in either solubility or vapor pressure, if such compounds compensate for the aberration in the other category and provide a superior insolubility in water or high vapor pressure or affinity to dissolve in the surfactant used.

It should also be noted that for medical uses, the gases should be biocompatible or not be physiologically deleterious. Ultimately, the microbubbles containing the gas phase will decay and the gas phase will be released into the blood either as a dissolved gas or as submicron droplets of the condensed liquid. It will be understood that gases will primarily be removed from the body through lung respiration or through a combination of respiration and other metabolic pathways in the reticuloendothelial system.

Other Components

It will be understood that other components can be included in the microbubble formulations of the present invention. For example, osmotic agents, stabilizers, chelators, buffers, viscosity modulators, air solubility modifiers, salts, and sugars can be added to fine tune the microbubble suspensions for maximum life and contrast enhancement effectiveness. Such considerations as sterility, isotonicity, and biocompatibility may govern the use of such conventional additives to injectable compositions. The use of such agents will be understood to those of ordinary skill in the art and the specific quantities, ratios, and types of agents can be determined empirically without undue experimentation.

Formation of the Microbubbles of the Present Invention.

There are a variety of methods which can be used to prepare microbubbles in accordance with the present invention. Rehydration of spray dried hollow microspheres is preferred. Sonication is also a preferred method for the formation of microbubbles, i.e., through an ultrasound transmitting septum or by penetrating a septum with an ultrasound probe including an ultrasonically vibrating hypodermic needle. However, it will be appreciated that a variety of other techniques exist for bubble formation. For example, gas injection techniques can be used, such as venturi gas injection.

Other methods for forming microbubbles include formation of particulate microspheres through the ultrasonication of albumin or other protein as described in European Patent Application 0,359,246 by Molecular Biosystems, Inc.; the use of tensides and viscosity increasing agents as described in U.S. Pat. No. 4,446,442; lipid coated, non-liposomal, microbubbles as is described in U.S. Pat. No. 4,684,479; liposomes having entrapped gases as is described in U.S. Pat. Nos. 5,088,499 and 5,123,414; and the use of denatured albumin particulate microspheres as is described in U.S. Pat. No. 4,718,433. The disclosure of each of the foregoing patents and applications is hereby incorporated by reference.

Sonication can be accomplished in a number of ways. For example, a vial containing a surfactant solution and gas in the headspace of the vial can be sonicated through a thin membrane. Preferably, the membrane is less than about 0.5 or 0.4 mm thick, and more preferably less than about 0.3 or even 0.2 mm thick, i.e., thinner than the wavelength of ultrasound in the material, in order to provide acceptable transmission and minimize membrane heating. The membrane can be made of materials such as rubber, Teflon, mylar, urethane, aluminized film, or any other sonically transparent synthetic or natural polymer film or film forming material. The sonication can be done by contacting or even depressing the membrane with an ultrasonic probe or with a focused ultrasound "beam." The ultrasonic probe can be disposable. In either event, the probe can be placed against or inserted through the membrane and into the liquid. Once the sonication is accomplished, the microbubble solution can be withdrawn from the vial and delivered to the patient.

Sonication can also be done within a syringe with a low power ultrasonically vibrated aspirating assembly on the syringe, similar to an inkjet printer. Also, a syringe or vial may be placed in and sonicated within a low power ultrasonic bath that focuses its energy at a point within the container.

Other types of mechanical formation of microbubbles are also contemplated. For example, bubbles can be formed with a mechanical high shear valve (or double syringe needle) and two syringes, or an aspirator assembly on a syringe. Even simple shaking may be used. The shrinking bubble techniques described herein are particularly suitable for mechanically formed bubbles, having lower energy input than sonicated bubbles. Such bubbles will typically have a diameter much larger than the ultimately desired biocompatible imaging agent, but can be made to shrink to an appropriate size by the loss of non-osmotic gases, thus concentrating the osmotic agent to near saturation.

In another method, microbubbles can be formed through the use of a liquid osmotic agent emulsion supersaturated with a modifier gas at elevated pressure introduced into a surfactant solution. This production method works similarly to the opening of soda pop, where the gas foams upon release of pressure, forming the bubbles.

In another method, bubbles can be formed similar to the foaming of shaving cream, using perfluorobutane, freon, or another like material that boils when pressure is released. However, in this method it is imperative that the emulsified liquid boils at sufficiently low temperatures or that it contain numerous bubble nucleation sites so as to prevent superheating and supersaturation of the aqueous phase. This supersaturation will lead to the generation of a small number of large bubbles on a limited number of nucleation sites rather than the desired large number of small bubbles (one for each droplet).

In still another method, dry void-containing particles or other structures (such as hollow spheres or honeycombs) that rapidly dissolve or hydrate, preferably in an aqueous solution, e.g., albumin, microfine sugar crystals, hollow spray dried sugar, salts, hollow surfactant spheres, dried porous polymer spheres, dried porous hyaluronic acid, or substituted hyaluronic acid spheres, or even commercially available dried lactose microspheres can be used to form the microbubbles of the present invention.

For example, a spray dried surfactant solution can be formulated by atomizing a surfactant solution into a heated gas such as air, carbon dioxide, nitrogen, or the like to obtain dried 1–10 micron or larger hollow or porous spheres, which are packaged in a vial filled with an osmotic gas or a desired gas mixture as described herein. The gas will diffuse into the voids of the spheres. Diffusion can be aided by pressure or vacuum cycling. When reconstituted with a sterile solution the spheres will rapidly dissolve and leave osmotic gas stabilized bubbles in the vial. In addition, the inclusion of starch or dextrins, a sugar polyester and/or an inflating agent such as methylene chloride, 1,1,2-trichlorotrifluoroethane (FREON 113, EM Science, Gibbstown, N.J.) or perfluorohexane, will result in microbubbles with an increased in vivo half-life. Particularly preferred starches for use in formation of microbubbles include those with a molecular weight of greater than about 500,000 daltons or a dextrose equivalency (DE) value of less than about 12. The DE value is a quantitative measurement of the degree of starch polymer hydrolysis. It is a measure of reducing power compared to a dextrose standard of 100. The higher the DE value, the greater the extent of starch hydrolysis. Such preferred starches include food grade vegetable starches of the type commercially available in the food industry, including those sold under the trademarks N-LOK and CAPSULE by National Starch and Chemical Co., (Bridgewater, N.J.); derivatized starches, such as hydroxyethyl starch (available under the trademarks HETASTARCH and HESPAN from du Pont Pharmaceuticals) (M-Hydroxyethylstarch, Ajinimoto, Tokyo, Japan). (Note that short chain starches spray dry well and can be used to produce microbubbles, but are not preferred because those with a molecular weight less than about 500,000 do not stabilize the microbubbles. However, they can be used in the present invention in applications in which additional stabilization is not required.) In the alternative, a lyophilized cake of surfactant and bulking reagents produced with a fine pore structure can be placed in a vial with a sterile solution and a head spaced with an osmotic gas mixture. The solution can be frozen rapidly to produce a fine ice crystal structure and, therefore, upon lyophilization produces fine pores (voids where the ice crystals were removed).

Alternatively, any dissolvable or soluble void-forming structures may be used. In this embodiment, where the void-forming material is not made from or does not contain surfactant, both surfactant and liquid are supplied into the container with the structures and the desired gas or gases. Upon reconstitution these voids trap the osmotic gas and, with the dissolution of the solid cake, form microbubbles with the gas or gases in them.

The microbubbles for use in the present invention can be formed -using a container enclosing the gas or gases described above for forming the microbubbles, the liquid, and the surfactant. The container can contain all of the sterile dry components, and the gas, in one chamber, with the sterile aqueous liquid in a second chamber of the same container. Suitable two-chamber vial containers are available, for example, under the trademarks WHEATON RS177FLW or S-1702FL from Wheaton Glass Co., (Millville, N.J.).

Alternatively, an inverted two-chamber vial may be used for microbubble preparation. One advantage associated with this method of microbubble formation is that the aqueous phase can be instilled first and sterilized via autoclaving or other means, followed by instillation of the spray dried microspheres. This will prevent potential microbial growth in the aqueous phase prior to sterilization.

Other suitable devices are known and are commercially available. For example, a two compartment glass syringe such as the B-D HYPAK Liquid/Dry 5+5 ml Dual Chamber prefilled syringe system (Becton Dickinson, Franklin Lakes, NJ; described in U.S. Pat. No. 4,613,326) can advantageously be used to reconstitute the spray dried powder.

It can be appreciated by one of ordinary skill in the art that other two-chamber reconstitution systems capable of combining the spray dried powder with the aqueous solution in a sterile manner are also within the scope of the present invention. In such systems, it is particularly advantageous if the aqueous phase can be interposed between the water-insoluble osmotic gas and the environment, to increase shelf life of the product.

Alternatively, the container can contain the void forming material and the gas or gases, and the surfactant and liquid can be added to form the microbubbles. In one embodiment, the surfactant can be present with the other materials in the container, so that only the liquid needs to be added in order to form the microbubbles. Where a material necessary for forming the microbubbles is not already present in the container, it can be packaged with the other components of a kit, preferably in a form or container adapted to facilitate ready combination with the other components of the kit.

The container used in the kit may be of the type described elsewhere herein. In one embodiment, the container is a conventional septum-sealed vial. In another, it has a means for directing or permitting application of sufficient bubble forming energy into the contents of the container. This means can comprise, for example, the thin web or sheet described previously.

The inclusion of the surfactants and wetting agents into the shell of the microsphere allows the use of a lower surfactant concentration. As the microsphere shell is dissolving, it temporarily surrounds the microbubble formed in its interior with a layer of aqueous phase that is saturated with the surfactants, enhancing their deposition on the microbubble's surface. Thus, spray-dried surfactant containing microspheres require only locally high concentrations of surfactant, and obviate the need for a high surfactant concentration in the entire aqueous phase.

Imaging Methodology

Any of the microbubble preparations of the present invention may be administered to a vertebrate, such as a bird or a mammal, as a contrast agent for ultrasonically imaging portions of the vertebrate. Preferably, the vertebrate is a human, and the portion that is imaged is the vasculature of the vertebrate. In this embodiment, a small quantity of microbubbles (e.g., 0.1 ml/Kg based on the body weight of the vertebrate) is introduced intravascularly into the animal. Other quantities of microbubbles, such as from about 0.005 ml/Kg to about 1.0 ml/Kg, can also be used. The heart, arteries, veins, and organs rich in blood, such as liver and kidneys can be ultrasonically imaged with this technique. Assuming that the ultrasound imaging machine is set to image at a particular frequency, the outgoing waveform supplied to the sonic transducer can be a numerical fraction of the imaging frequency (e.g., 1/2, 2/3, 1/3, and the like) or a whole number or fractional multiple of the imaging frequency (e.g., 2, 3/2, 3, 4, and the like). With any particular combination of microbubble composition and excitation frequency, certain harmonics will be dominant. The second harmonic is a common example. Those strongest harmonics are preferred for obvious reasons, although other harmonics may be selected for reasons such as preparation of multiple images or elimination of background. Dominant harmonics can be determined by simple empirical testing of the microbubble solution.

The foregoing description will be more fully understood with reference to the following Examples. Such Examples, are, however, exemplary of preferred methods of practicing the present invention and are not limiting of the scope of the invention or the claims appended hereto.

EXAMPLE 1

Preparation of Ultrasound Contrast Agent Through Sonication

Microbubbles with an average number weighted size of 5 microns were prepared by sonication of an isotonic aqueous phase containing 2% the block copolymer PLURONIC F-68 and 1% sucrose stearate as surfactants, air as a modifier gas and perfluorohexane at a concentration near saturation at 37° C. 1.3 ml of a sterile water solution containing 0.9% NaCl, 2% the block copolymer PLURONIC F-68 and 1% sucrose stearate was added to a 2.0 ml vial. The vial had a remaining head space of 0.7 ml initially containing air. Air saturated with perfluorohexane vapor (220 mmHg of perfluorohexane with 540 mmHg of air) at 25° C. was used to flush the headspace of the vial. The vial was sealed with a thin 0.22 mm polytetrafluoroethylene (PTFE) septum. The vial was turned horizontally, and a ⅛" (3 mm) sonication probe attached to a 50 watt sonicator model VC50, available from Sonics & Materials, was pressed gently against the septum. In this position, the septum separates the probe from the solution. Power was then applied to the probe and the solution was sonicated for 15 seconds, forming a white solution of finely divided microbubbles, having an average number weighted size of 5 microns as measured by Horiba LA-700 laser light scattering particle analyzer.

EXAMPLE 2

Use of Sonicated Contrast Agent

Two rabbits were injected with doses ranging from 0.1 to 0.3 ml of contrast agent prepared according to Example 1 for a total of 5 injections per rabbit. The rabbits were then imaged with an experimental ultrasound instrument at the University of Toronto, Sunnybrook Health Science Center, 2075 Bayview Avenue, North York, Ontario, Canada. This instrument was capable of imaging in normal gray-scale and Doppler modes as well as harmonic enhanced gray-scale and Doppler modes. Images of the heart, interior vena cava, aorta, kidneys and liver were examined. Images of the rabbit were greatly enhanced when this contrast agent was injected while imaging in the harmonic enhanced modes. Small vessels were clearly visible after contrast injection, while the nonvascular clutter signals were greatly reduced. This enhancement lasted approximately 2 to 3 minutes. The enhanced image was the result of the contrast agent generating superior harmonic ultrasound signals.

EXAMPLE 3

Preparation of Formula 1

Spray Dried Ultrasound Contrast Agent

One liter of each of the following solutions was prepared with water for injection: Solution A containing 4.0% w/v N-Lok vegetable starch (National Starch and Chemical Co., Bridgewater, N.J.) and 1.9% w/v sodium chloride (Mallinckrodt, St. Louis, Mo.) and Solution B containing 2.0% Superonic F-68 (Serva, Heidelberg, Germany) and 2.0% w/v Ryoto Sucrose Stearate S-1670 (Mitsubishi-Kasei Food Corp., Tokyo, Japan). Solution B was added to a high shear mixer and cooled in an ice bath. A coarse suspension of 40 ml 1,1,2-trichlorotrifluoroethane (FREON 113; EM Science, Gibbstown, N.J.) was made in the 1 liter of solution B. This suspension was emulsified using a Microfluidizer (Microfluidics Corporation, Newton, Mass.; model M-110F) at 10,000 psi, 5° C. for 5 passes. The resulting emulsion was added to solution A to produce the following formula for spray drying:

2.0* w/v m-HES hydroxyethylstarch (Ajinimoto, Tokyo, Japan)
2.0% w/v sodium chloride (Mallinckrodt)
0.87% sodium phosphate, dibasic (Mallinckrodt)
0.26% sodium phosphate, monobasic (Mallinckrodt)
1.7* w/v Superonic F-68 (Serva)
0.3% w/v Sucrose Stearate S-1670 (Mitsubishi-Kasei Food Corp.)
0.1% w/v Sucrose Stearate S-570 (Mitsubishi-Kasei Food Corp.)
4.0% w/v 1,1,2-trichlorotrifluoroethane (FREON 113; EM Science)

This emulsion was then spray dried in a Niro Atomizer Portable Spray Dryer equipped with a two fluid atomizer (Niro Atomizer, Copenhagen, Denmark) employing the following settings:

hot air flow rate=39.5 CFM
inlet air temp.=255° C.
outlet air temp.=109° C.
atomizer air flow=110 liters/min
emulsion feed rate=1 liter/hr The dry, hollow spherical product had a diameter between about 1 $\mu M$ and about 15 $\mu M$ and was collected at the cyclone separator as is standard for this dryer. Aliquots of powder (250 mg) were weighed into 10 ml tubing vials, sparged with perfluorohexane-saturated nitrogen (2 mg perfluorohexane per ml of gas) at 13° C. and sealed. The nitrogen was saturated with perfluorohexane by passing it through three perfluorohexane filled gas washing bottles immersed in a 13° C. water bath.

The vials were reconstituted for injection with 5 ml water to 400 mg of spray dried powder after inserting an 18 -gauge needle as a vent to relieve pressure as the water was injected.

EXAMPLE 4

Use of Formula 1 Spray Dried

Ultrasound Contrast Agent

A 1 ml injection of the contrast agent prepared as described in Example 3 was administered to two rabbits. The rabbits were then imaged as described in Example 2 above.

The formula enhanced the harmonic signal generated by the microbubbles. The Formula #1 spray dried contrast agent produced greater enhancement than the sonicated contrast agent described in Example 1 above, and this enhancement lasted for approximately 4 minutes. This improved harmonic response and persistence are the results of a more optimally chosen non-Newtonian surfactant system. The formula demonstrated that a condensable vapor, an absorbable vapor, a non-Newtonian surfactant and a fluorocarbon vapor stabilized monolayer surfactant bubble, generate enhanced harmonics for superior in viva imaging.

EXAMPLE 5

Preparation of Formula 2

Spray Dried Ultrasound Contrast Agent

One liter of each of the following solutions was prepared with water for injection: Solution A containing 4.0% w/v N-Lok vegetable starch (National Starch and Chemical Co., Bridgewater, N.J.) and 1.9% w/v sodium chloride (Mallinckrodt, St. Louis, Mo.) and Solution B containing 2.0% Superonic F-68 (Serva, Heidelberg, Germany) and 2.0% w/v Ryoto Sucrose Stearate S-1670 (Mitsubishi-Kasei Food Corp., Tokyo, Japan). Solution B was added to a high shear mixer and cooled in an ice bath. A coarse suspension of 40 ml 1,1,2-trichlorotrifluoroethane (FREON 113; EM Science, Gibbstown, N.J.) was made in the 1 liter of solution B. This suspension was emulsified using a Microfluidizer (Microfluidics Corporation, Newton, Mass.; model M-110F) at 10,000 psi, 5° C. for 5 passes. The resulting emulsion was added to solution A to produce the following formula for spray drying:

- 2.0% w/v m-HES hydroxyethylstarch (Ajinimoto, Tokyo, Japan)
- 3.0% w/v sodium chloride (Mallinckrodt)
- 1.7% w/v Superonic F-68 (Serva)
- 0.2% w/v Sucrose Stearate S-1670 (Mitsubishi-Kasei Food Corp.)
- 0.1% w/v Sucrose Stearate S-570 (Mitsubishi-Kasei Food Corp.)
- 4.0% w/v 1,1,2-trichlorotrifluoroethane (FREON 113; EM Science)

This emulsion was then spray dried in a Niro Atomizer Portable Spray Dryer equipped with a two fluid atomizer (Niro Atomizer, Copenhagen, Denmark) employing the following settings:

- hot air flow rate=39.5 CFM
- inlet air temp.=220° C.
- outlet air temp.=103° C.
- atomizer air flow=110 liters/min
- emulsion feed rate=1 liter/hr The dry, hollow spherical product had a diameter between about 1 $\mu$M and about 15 $\mu$M and was collected at the cyclone separator as is standard for this dryer. Aliquots of powder (250 mg) were weighed into 10 ml tubing vials, sparged with perfluorohexane-saturated nitrogen (2 mg perfluorohexane per ml of gas) at 13° C. and sealed. The nitrogen was saturated with perfluorohexane by passing it through three perfluorohexane filled gas washing bottles immersed in a 13° C. water bath.

The vials were reconstituted for injection with 5 ml water to 350 mg of spray dried powder after inserting an 18-gauge needle as a vent to relieve pressure as the water was injected.

EXAMPLE 6

Use of Formula 2 Spray Dried

Ultrasound Contrast Agent

Two 1 ml injections of the contrast agent described in Example 5 was administered to two rabbits. The rabbits were then imaged as described in Example 2 above.

The formula enhanced the harmonic signal generated by the microbubbles. The Formula #2 spray dried contrast agent produced greater enhancement than the sonicated contrast agent described in Example 1 above and the Formula #1 spray dried contrast agent described in Example 3, and this enhancement lasted for approximately 5 minutes. This improved harmonic response and persistence are the results of an improved surfactant formulation. The formula again demonstrated that a condensable vapor, an absorbable vapor, a non-Newtonian surfactant and a fluorocarbon vapor stabilized monolayer surfactant bubble, generate enhanced harmonics for superior in vivo imaging.

EXAMPLE 7

Preparation of Formula 3

Spray Dried Ultrasound Contrast Agent

One liter of each of the following solutions was prepared with water for injection: Solution A containing 4.0% w/v N-Lok vegetable starch (National Starch and Chemical Co., Bridgewater, NJ) and 1.9% w/v sodium chloride (Mallinckrodt, St. Louis, Mo.) and Solution B containing 2.0% Superonic F-68 (Serva, Heidelberg, Germany) and 2.0% w/v Ryoto Sucrose Stearate S-1670 (Mitsubishi-Kasei Food Corp., Tokyo, Japan). Solution B was added to a high shear mixer and cooled in an ice bath. A coarse suspension of 40 ml 1,1,2-trichlorotrifluoroethane (FREON 113; EM Science, Gibbstown, N.J.) was made in the 1 liter of solution B. This suspension was emulsified using a Microfluidizer (Microfluidics Corporation, Newton, MA; model M-110F) at 10,000 psi, 5° C. for 5 passes. The resulting emulsion was added to solution A to produce the following formula for spray drying:

- 3.9% w/v m-HES hydroxyethylstarch (Ajinimoto, Tokyo, Japan)
- 3.25% w/v sodium chloride (Mallinckrodt)
- 2.83% sodium phosphate, dibasic (Mallinckrodt)
- 0.42% sodium phosphate, monobasic (Mallinckrodt)
- 2.11% w/v Superonic F-68 (Serva)
- 0.32% w/v Sucrose Stearate S-1670 (Mitsubishi-Kasei Food Corp.)
- 0.16% w/v Sucrose Stearate S-570 (Mitsubishi-Kasei Food Corp.)
- 3.0% w/v 1,1,2-trichlorotrifluoroethane (FREON 113; EM Science)

This emulsion was then spray dried in a Niro Atomizer Portable Spray Dryer equipped with a two fluid atomizer (Niro Atomizer, Copenhagen, Denmark) employing the following settings:

- hot air flow rate=31 CFM
- inlet air temp.=370° C.
- outlet air temp.=120° C.
- atomizer air flow=290 liters/min
- emulsion feed rate=1.5 liters/hr The dry, hollow spherical product had a diameter between about 1 $\mu$M and about 15 $\mu$M and was collected at the cyclone separator as is standard for this dryer. Aliquots of powder (250 mg) were weighed into 10 ml tubing vials, sparged with perfluorohexane-saturated nitrogen (2 mg perfluorohexane per ml of gas) at 13° C. and sealed. The nitrogen was saturated with perfluorohexane by passing it through three perfluorohexane filled gas washing bottles immersed in a 13° C. water bath.

The vials were reconstituted for injection with 5 ml water to 100 mg of spray dried powder after inserting an 18-gauge needle as a vent to relieve pressure as the water was injected.

EXAMPLE 8

Use of Formula 3 Spray Dried

Ultrasound Contrast Agent

An anesthetized dog weighing approximately 20 Kg was prepared for examination at the Mayo Clinic, 200 First Street Southwest, Rochester, Minn., with an experimental ultrasound imaging instrument capable of imaging in normal gray-scale and Doppler modes, as well as harmonic enhanced gray-scale and Doppler modes. This instrument was designed independently from the one used in the examples above. The heart of the dog was imaged in all modes before and after injection of 0.5 ml, 1.5 ml and 2 ml doses of the microbubble ultrasound contrast agent described in Example 7.

The harmonic enhanced mode images were far superior to the normal mode images in defining the motions of the heart wall, the volume of the chambers, and visualizing the contrast agent perfusing the heart muscle. Individual perforator vessels in the septum of the heart were observed. The contrast had a useful lifetime in the blood of approximately 5 minutes.

The experiments described above demonstrate the enhanced harmonic generation of a microbubble contrast agent that (1) contains perfluorohexane with a vapor pressure at 37° C. over 23 mmHg, less than 1% wt./wt. solubility in water, and present at a concentration in the gas greater than 2% mole fraction and above 50% of its saturation concentration that enhances harmonic generation by condensation; that (2) contains gas with more than 2% mole fraction of perfluorohexane that (a) has a solubility of its liquid phase in hexane at 37° C. of more than 10% mole/mole and (b) has a solubility of its liquid phase in water of less than 1% wt./wt. at 37° C., and therefore enhances harmonic generation by adsorbing/dissolving in the surfactant layer; that (3) contains a non-Newtonian surfactant that enhances harmonic generation; or that (4) contains microbubbles stabilized by perfluorohexane, a gas osmotic agent, and a monolayer of surfactant that enhances harmonic generation.

EXAMPLE 9

Use of Sonicated Ultrasound Contrast Agent

A microbubble contrast agent is prepared by sonication as in Example 1 above except that the atmosphere in the vial prior to sonication (and therefore the gas in the microbubbles) is 100% perfluorobutane and the solution in the sonicated vial is 0.9% saline plus 3% the block copolymer PLURONIC F-68 (a Newtonian water soluble surfactant that demonstrates only small changes in surface tension when the monolayer is compressed).

A rabbit is imaged as in Example 2 above after injecting 0.3 ml of this contrast agent. While the vascular persistence and harmonic generation of this preparation are not optimal, higher levels of harmonic enhancement are achieved, relative to air filled microbubbles, because of the ability of perfluorobutane to dissolve in or adsorb to the hydrophobic region of the the block copolymer PLURONIC F-68 monolayer. This is because perfluorobutane has a solubility in hexane of greater than 10% mole/mole and a water solubility of less than 1% wt./wt. In addition, the bubbles are stabilized by their gas contents and have a monolayer of surfactant.

EXAMPLE 10

Use of Sonicated Ultrasound Contrast Agent

The contrast agent described in Example 9 is made with bubbles containing nitrogen saturated with perfluorohexane at 13° C. Rabbits are imaged using the contrast agent as described above. The harmonic enhancement of this formulation is better than in Example 9 because, in addition to the adsorption and gas stabilized monolayer effects described in Example 9, the perfluorohexane can condense when excited, e.g., it is present in more than 2% mole fraction of the gas phase and at a concentration above 50% of its saturation concentration, is less than 1% wt./wt. soluble in water, and has a vapor pressure at 37° C. over 23 mmHg.

EXAMPLE 11

Use of Ultrasound Contrast Agent

Containing Albumin-Coated Microbubbles

The commercial available microbubble preparation Albunex (Molecular Biosystems Inc., San Diego, Calif.) is prepared employing nitrogen saturated with perfluorohexane at 13° C. as the gas mixture present during the formation of the bubbles by sonication according to the method described in U.S. Pat. No. 4,957,656. This contrast agent is injected into a rabbit and imaged as in Example 2 above. Even though this agent is damped by many layers of albumin surfactant and does not contain a non-Newtonian surfactant, its harmonic enhancement is increased by the presence of perfluorohexane which will condense and adsorb during excitation, producing enhanced ultrasound images.

EXAMPLE 12

Use of Ultrasound Contrast Agent Containing Fluorinated

Surfactant with Liquid Perfluoropentane Emulsions

A perfluoropentane emulsion is prepared according to the method disclosed in Example 42 of Quay, PCT application number PCT/US94/00422. The emulsion is administered to a rabbit which is imaged as described in Example 2 above, employing harmonic enhanced modes. Upon injection, this perfluoropentane emulsion boils at the body temperature of the rabbit to form microbubbles containing approximately 100% perfluoropentane gas. This gas will condense under excitation as described in the foregoing disclosure, generating enhanced harmonic signals.

The solubility of perfluoropentane in water and hexane meet the criteria above for adsorption in the surfactant layer of the microbubble, generating enhanced harmonic signals. This preparation also contains ZONYL FSO surfactant, a fluorinated non-Newtonian surfactant available from E.I. Du Pont, whose surface tension changes rapidly when the monolayer is compressed, generating enhanced harmonic signals. The surfactant mixture employed in the contrast agent (the block copolymer PLURONIC P-123 and the fluorosurfactant ZONYL FSO) is one that forms monolayers on bubbles and the bubble is stabilized by its gas contents, therefore avoiding damping of the volume oscillations of the bubble when excited, and resulting in enhanced harmonic signal generation.

The foregoing description details certain preferred embodiments of the present invention and describes the best mode contemplated. It will be appreciated, however, that no matter how detailed the foregoing appears in text, the invention can be practiced in many ways and the invention should be construed in accordance with the appended claims and any equivalents thereof.

What is claimed is:

1. A method for harmonic ultrasonic imaging of an object or body comprising the steps of:
    introducing into said object or body a contrast agent comprising a plurality of osmotically stabilized microbubbles comprising at least one gas that is not air, wherein said contrast agent comprises a phospholipid and which, when insonated with a fundamental frequency, radiates ultrasonic energy at frequencies other than the fundamental frequency; and imaging at least a portion of said object or body utilizing at least one frequency other than said fundamental frequency.

2. The method of claim 1 wherein said phospholipid comprises phosphatidyl choline.

3. The method of claim 1 wherein said microbubbles comprise a generally spherical membrane.

4. The method of claim 3 wherein said membrane comprises said phospholipid.

5. The method of claim 4 wherein said membrane comprises a monolayer.

6. The method of claim 4 wherein said membrane further comprises a surfactant.

7. The method of claim 6 wherein the surfactant is selected from the group consisting of sugar esters, block copolymers, zonyl surfactants and combinations thereof.

8. The method of claim 1 wherein said microbubbles comprise at least one gas or vapor selected from the group consisting of fluorocarbons, hydrocarbons and mixtures thereof.

9. The method of claim 8 wherein said microbubbles further comprise a gas or vapor selected from the group consisting of perfluorohexane, perfluoropentane, perfluorocyclopentane, 1,1,2-trichlorotrifluoroethane, cyclopentane, methylene chloride, pentane, hexane, dichlorodiluoromethane, trichloromonofluoromethane, perfluorobutane, perfluorocyclobutane, perfluoropropane, butane, cyclobutane, propane, methane, and ethane.

10. The method of claim 8 wherein said gas or vapor comprises a perfluoropropane.

11. The method of claim 8 wherein said gas or vapor comprises a perfluorobutane.

12. The method of claim 8 wherein said gas or vapor comprises a perfluorohexane.

13. The method of claim 8 wherein said gas or vapor comprises a Freon.

14. The method of claim 1 wherein said microbubbles comprise sulfur hexafluoride.

15. The method of claim 1 wherein said microbubbles comprise a gas or vapor comprising at least one gas osmotic agent and at least one modifier gas.

16. The method of claim 15 wherein said modifier gas is selected from the group consisting of nitrogen, oxygen, carbon dioxide and mixtures thereof.

17. The method of claim 16 wherein said gas osmotic agent is perfluorohexane.

18. The method of claim 1 wherein said contrast agent comprises a plurality of liposomes.

19. The method of claim 18 wherein said microbubbles comprise at least one gas or vapor selected from the group consisting of fluorocarbons, hydrocarbons and mixtures thereof.

20. The method of claim 19 wherein said microbubbles further comprise a gas or vapor is selected from the group consisting of perfluorohexane, perfluoropentane, perfluorocyclopentane, 1,1,2-trichlorotrifluoroethane, cyclopentane, methylene chloride, pentane, hexane, dichlorodiluoromethane, trichloromonofluoromethane, perfluorobutane, perfluorocyclobutane, perfluoropropane, butane, cyclobutane, propane, methane, and ethane.

21. The method of claim 19 wherein said gas or vapor comprises perfluoropropane.

22. The method of claim 19 wherein said gas or vapor comprises perfluorobutane.

23. The method of claim 19 wherein said gas or vapor comprises a perfluorohexane.

24. The method of claim 19 wherein said gas or vapor comprises a Freon.

25. The method of claim 18 wherein said microbubbles comprise sulfur hexafluoride.

26. The method of claim 18 wherein said microbubbles comprise a gas or vapor comprising at least one gas osmotic agent and at least one modifier gas.

27. The method of claim 26 wherein said modifier gas is selected from the group consisting of nitrogen, oxygen, carbon dioxide and mixtures thereof.

28. The method of claim 1 wherein said plurality of microbubbles comprise a phospholipid microbubble membrane enclosing perfluoropropane.

29. The method of claim 1 wherein said plurality of microbubbles comprise a phospholipid microbubble, membrane enclosing perfluorobutane.

30. The method of claim 1 wherein said plurality of microbubbles comprise a phospholipid microbubble membrane enclosing a gaseous mixture comprising perfluorohexane and nitrogen.

31. A method for harmonic ultrasonic imaging of an object or body comprising the steps of:

introducing into said object or body a contrast agent comprising a plurality of osmotically stabilized microbubbles comprising at least one gas that is not air, wherein said contrast agent comprises a fluorinated surfactant and which, when insonated with a fundamental frequency, radiates ultrasonic energy at frequencies other than the fundamental frequency; and imaging at least a portion of said object or body utilizing at least one frequency other than said fundamental frequency.

32. The method of claim 31 wherein said microbubbles comprise perfluoropentane.

33. A method for harmonic ultrasonic imaging of an object or body comprising the steps of:

introducing into said object or body a contrast agent comprising a plurality of osmotically stabilized microbubbles comprising at least one gas that is not air, wherein said contrast agent comprises a protein and which, when insonated with a fundamental frequency, radiates ultrasonic energy at frequencies other than the fundamental frequency; and imaging at least a portion of said object or body utilizing at least one frequency other than said fundamental frequency.

34. The method of claim 33 wherein said protein comprises albumin.

35. The method of claim 34 wherein said microbubbles further comprise a fluorocarbon gas or vapor.

36. The method of claim 35 wherein said fluorocarbon gas or vapor comprises perfluoropropane.

37. The method of claim 35 wherein said fluorocarbon gas or vapor comprises perfluorobutane.

38. The method of claim 35 wherein said fluorocarbon gas or vapor comprises perfluoropentane.

39. The method of claim 35 wherein said fluorocarbon gas or vapor comprises perfluorohexane.

* * * * *